(12) United States Patent
Nomori

(10) Patent No.: US 7,156,090 B2
(45) Date of Patent: Jan. 2, 2007

(54) TRACHEOSTOMY TUBE

(76) Inventor: Hiroaki Nomori, 1-2-51-303, Kamitakada, Nakano-ku, Tokyo (JP)

( * ) Notice: Subject to any disclaimer, the term of this patent is extended or adjusted under 35 U.S.C. 154(b) by 0 days.

(21) Appl. No.: 10/345,924

(22) Filed: Jan. 17, 2003

(65) Prior Publication Data

US 2003/0136412 A1 Jul. 24, 2003

(30) Foreign Application Priority Data

Jan. 21, 2002 (JP) .............................. 2002-012066

(51) Int. Cl.
*A61M 16/00* (2006.01)

(52) U.S. Cl. .......................... 128/200.26; 128/207.15; 128/207.29

(58) Field of Classification Search .......... 128/200.26, 128/207.14, 207.15, 207.29; 623/9; 604/99.01, 604/102.01, 103.01

See application file for complete search history.

(56) References Cited

U.S. PATENT DOCUMENTS

| | | | | |
|---|---|---|---|---|
| 2,804,076 | A * | 8/1957 | Giraudon | 128/207.16 |
| 3,066,674 | A * | 12/1962 | Capra | 128/207.16 |
| 3,402,718 | A * | 9/1968 | Doherty | 128/207.15 |
| 3,460,541 | A * | 8/1969 | Doherty | 128/207.15 |
| 3,481,339 | A * | 12/1969 | Puig | 128/207.15 |
| 3,565,079 | A * | 2/1971 | Jackson | 128/207.15 |
| 3,616,799 | A * | 11/1971 | Sparks | 128/207.15 |
| 3,659,612 | A * | 5/1972 | Shiley et al. | 128/207.15 |
| 3,707,151 | A * | 12/1972 | Jackson | 128/207.15 |
| 3,709,227 | A * | 1/1973 | Hayward | 128/207.15 |
| 3,734,100 | A * | 5/1973 | Walker et al. | 128/207.15 |
| 3,769,983 | A * | 11/1973 | Merav | 128/207.15 |
| 3,794,026 | A | 2/1974 | Jacobs | |
| 3,995,643 | A * | 12/1976 | Merav | 128/207.15 |
| 4,037,605 | A * | 7/1977 | Firth | 128/207.15 |
| 4,278,081 | A * | 7/1981 | Jones | 128/207.15 |
| 4,280,492 | A * | 7/1981 | Latham | 128/207.15 |
| 4,449,523 | A * | 5/1984 | Szachowicz et al. | 128/200.26 |
| 4,459,984 | A * | 7/1984 | Liegner | 128/207.15 |
| 4,572,186 | A * | 2/1986 | Gould et al. | 606/194 |
| 4,596,248 | A * | 6/1986 | Lieberman | 128/207.16 |
| 4,633,864 | A * | 1/1987 | Walsh | 128/207.15 |
| 4,821,722 | A * | 4/1989 | Miller et al. | 606/192 |
| 4,852,565 | A * | 8/1989 | Eisele | 128/207.14 |
| 4,979,505 | A * | 12/1990 | Cox | 128/207.15 |
| 5,054,484 | A * | 10/1991 | Hebeler, Jr. | 128/207.16 |
| 5,056,515 | A * | 10/1991 | Abel | 128/207.15 |
| 5,100,384 | A * | 3/1992 | McBrien et al. | 604/99.01 |
| 5,318,021 | A | 6/1994 | Alessi | |
| 5,342,303 | A * | 8/1994 | Ghaerzadeh | 604/102.01 |
| 5,419,314 | A * | 5/1995 | Christopher | 128/200.26 |

(Continued)

FOREIGN PATENT DOCUMENTS

GB 1153863 5/1969

(Continued)

*Primary Examiner*—Aaron J. Lewis
(74) *Attorney, Agent, or Firm*—Wenderoth, Lind & Ponack, L.L.P.

(57) ABSTRACT

A tracheostomy tube that enables speech. The tube is provided with an inside tube portion to be set in a trachea, an outside tube portion connected to a ventilator, and a balloon provided on the outer circumference of the inside tube portion. The balloon is connected to the inside tube portion so that the inside and outside of the balloon cannot communicate with each other and the inside tube portion has a hole for communicating the inside of the interior of the inside tube portion with the inside of the balloon.

6 Claims, 2 Drawing Sheets

U.S. PATENT DOCUMENTS 5,458,139 A * 10/1995 Pearl ................... 128/207.14
5,771,888 A * 6/1998 Keim ................... 128/207.15
5,957,978 A * 9/1999 Blom ............................. 623/9
6,569,145 B1 * 5/2003 Shmulewitz et al. ....... 604/509
6,827,703 B1 * 12/2004 Ackerman ............... 604/96.01
2001/0041861 A1 * 11/2001 Gobel ..................... 604/99.01

FOREIGN PATENT DOCUMENTS

WO          01/10490          2/2001

* cited by examiner

TRACHEOSTOMY TUBE

FIELD OF THE INVENTION

The present invention relates to a tracheostomy tube, particularly to a tracheostomy tube enabling speech.

BACKGROUND OF THE INVENTION

The artificial ventilation using a normal tracheostomy tube is a method of supplying oxygen or air through a ventilator by dissecting the trachea of a cervical part, inserting a balloon-provided tube into a trachea to connect the tube with the ventilator, supplying air into the balloon, and contact-bonding the balloon with an inner wall so that oxygen or air does not flow toward a mouth.

In the case of this method, the balloon is always inflated and thereby the gap between the trachea and the tube is blocked so that the air for respiration reciprocates only between the ventilator and a lung. Otherwise, when supplying air, most air does not reach the lung but it leaks to the mouth, and thus artificial ventilation cannot be performed.

As described above, when using a conventional tracheostomy tube, air reciprocates only between a ventilator and a lung. Because a vocal cord is located between a trachea and a mouth, it is impossible to supply air to the vocal cord and thereby, a patient is unable to speak when using the conventional tracheostomy tube.

As described above, the present invention is made by considering the prior art and its object is to provide a tracheostomy tube enabling speech.

SUMMARY OF THE INVENTION

To solve the above technical problems of the prior art, the present invention provides a tracheostomy tube comprising an inside tube portion to be set in a trachea, an outside tube portion to be connected to a ventilator, and a balloon set on the circumference of the inside tube portion, characterized in that the balloon is set to the outside of the inside tube portion so that the inside and outside of the balloon cannot communicate with each other, and the inside tube portion has a hole for communicating the inside of the inside tube portion with the inside of the balloon.

A tracheostomy tube of the present invention is constructed so that air is supplied to the inside of a balloon from a ventilator through a hole formed on an inside tube portion in the case of inspiration, that is, when a ventilator supplies air, the balloon inflates, the gap between a trachea and a tube is blocked, and the air supplied from the ventilator enters a lung without leaking. In the case of expiration, that is, exhaling, the air inside the balloon returns to the inside of the inside tube portion through a hole formed on the inside tube portion and the balloon contracts to the original size so as to contact with the outer wall of the inside tube portion. Therefore, a gap is formed between tube and the trachea and some of exhaled air flows to the outside of a patient through his (or her) vocal cord. Thereby, the tube enables patients to speak during mechanical ventilation.

DETAILED DESCRIPTION OF THE INVENTION

Figure 1:
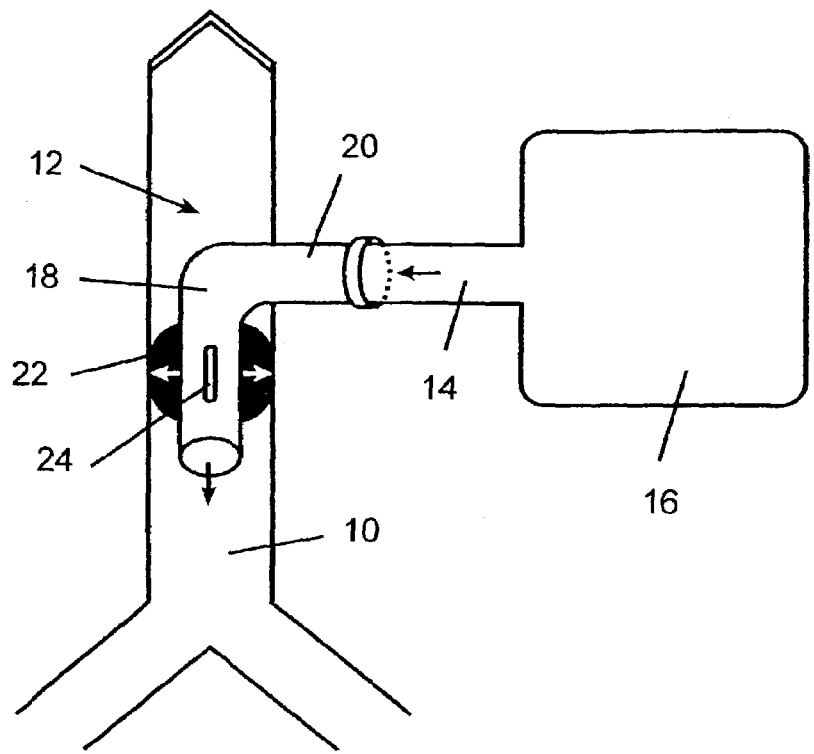
FIG. 1 is a schematic view showing a tracheostomy tube under an inspiration state according to a preferred embodiment of the present invention.
Figure 2:
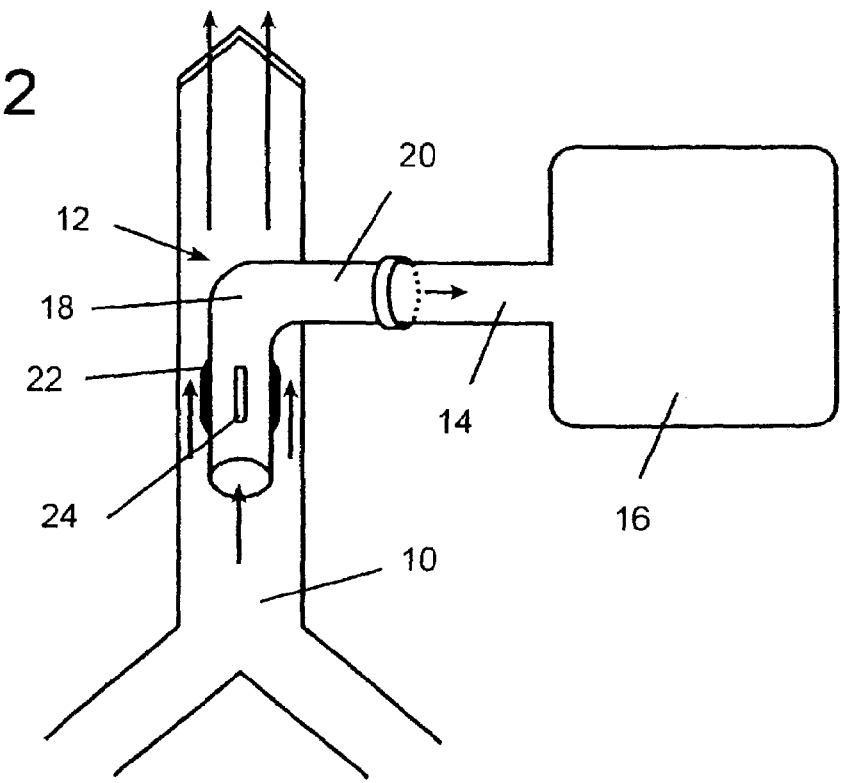
FIG. 2 is a schematic view showing a tracheostomy tube under an expiration state according to a preferred embodiment of the present invention.

FIGS. 1 and 2 show a tracheostomy tube 12 according to a preferred embodiment of the present invention set in the trachea 10 of a patient, in which FIG. 1 shows an inspiration state and FIG. 2 shows an expiration state.

The tracheostomy tube 12 is provided with an inside tube portion 18 to be set in a trachea, an outside tube portion 20 to be connected to a ventiator 16, and a balloon 22 set on the circumference of the outside of an inside tube portion.

The balloon 22 is connected to the outer wall of the inside tube portion 18 over the circumference of the inside tube portion 18 by an adhesive or the like at the upper and lower portions of the balloon 22 so that the inside and outside of the balloon 22 do not communicate with each other.

Figure 3:
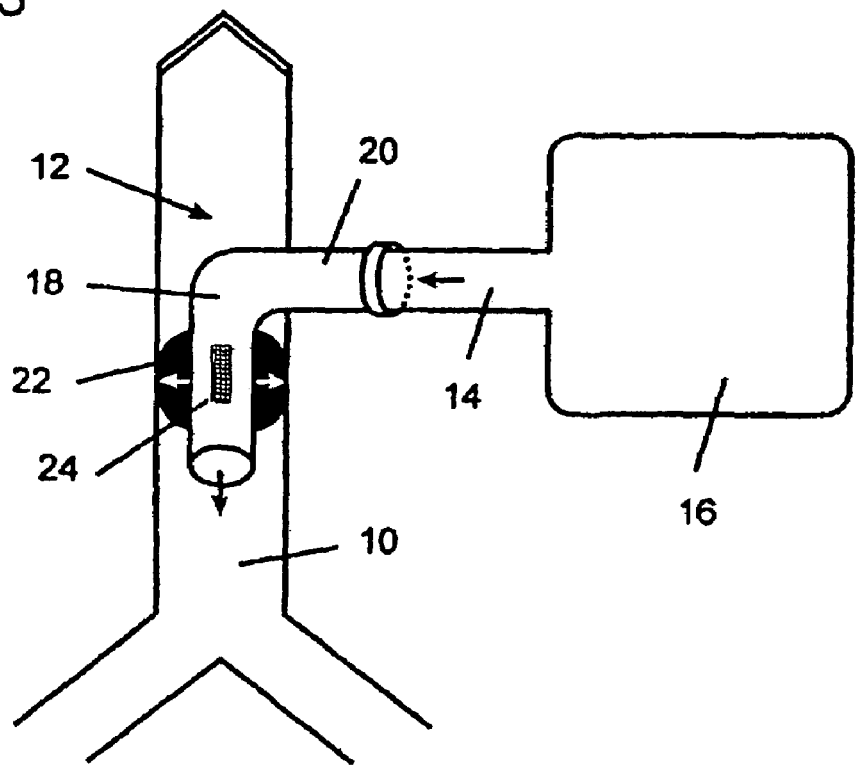
FIGS. 3–4 are schematic views, similar to FIGS. 1–2, but show a tracheostomy tube with an opening formed as a mesh.
Figure 4:
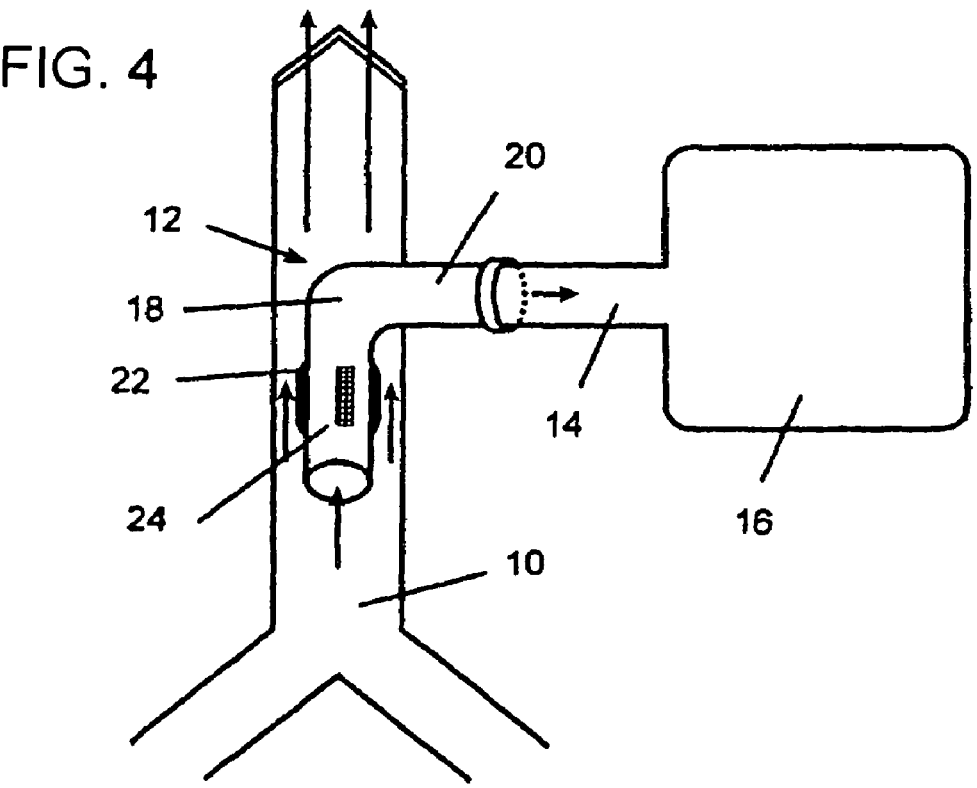

The inside tube portion 18 has a hole 24 for communicating the inside of the inside tube portion 18 with the inside of the balloon 22. The hole 24 is formed like an opening such as an aperture, slit, mesh (see FIGS. 3–4), or columnar structure.

The ventilator 16 repeats inspiration and expiration at a predetermined cycle. The ventilator 16 discharges a predetermined quantity of oxygen or air at a predetermined pressure in the case of inspiration and communicates the inside of the tracheostomy tube 12 with atmosphere or attracts the gas in the tracheostomy tube 12 at a treatment pressure.

The tracheostomy tube 12 is constituted as described above. Therefore, when oxygen or air is supplied into the tracheostomy tube 12 by the ventilator 16 in the case of inspiration, air is supplied into the inside of the balloon 22 through the hole 24 of the inside tube portion 18, the balloon 22 inflates and the outer face of the balloon 22 make contact with the side face (wall) of the trachea 10 to inhibit communication between the lung side and entrance side of the trachea. Thereby, it is possible to effectively supply oxygen or air into the lung of a patient without air leakage.

In the case of expiration, the air in the balloon 22 returns to the inside of the inside tube portion 18 through the hole 24 formed on the inside tube portion 18 and the balloon 22 contracts to the original size so as to make contact with the outer wall of the inside tube portion 18. Therefore, a gap is formed between the tracheostomy tube 12 and the trachea 10 and some of exhaled air flows to the outside of a patient through his (or her) vocal cord. Thereby, the patient's speech enabled. trachea 10 and some of exhaled air flows to the outside of a patient through his (or her) vocal cord. Thereby, the patient's speech enabled.

The invention claimed is:

1. A tracheostomy tube for enabling speech by a patient, said tracheostomy tube comprising:
    a hollow tube having an inside tube portion for being located in a trachea, and an outside tube portion adapted to be connected to a ventilator; and
    a balloon provided on an outer circumferential surface of the inside tube portion, wherein said hollow tube has at least one opening formed in a wall of the inside tube portion, and said balloon is connected to the outer circumferential surface of the inside tube portion above and below the opening so that air can communicate with an interior of the balloon only through the opening, wherein said opening is formed as a mesh, and wherein said balloon is adapted to inflate during inspiration to block a gap between a trachea and the outer circumferential surface of the inside tube portion, and to contract during expiration so as to contact the outer circumferential surface of the inside tube portion so as to allow speech by the patient.

2. A tracheostomy tube as claimed in claim 1, wherein said balloon forms a solid wall between the connection locations of said balloon above and below the opening formed in said inside tube portion.

3. The tracheostomy tube as claimed in claim 1, wherein, during expiration, substantially the entire opposing surface of the balloon is in contact with the outer circumferential surface of the inside tube portion.

4. A tracheostomy tube for enabling speech by a patient, said tracheostomy tube comprising:

a hollow tube having an inside tube portion for being located in a trachea, and an outside tube portion adapted to be connected to a ventilator; and a balloon secured to an outer circumferential surface of the inside tube portion so as to define an inflatable annular chamber surrounding said hollow tube, wherein, when the inside tube portion is located in the trachea and air is supplied through the outside tube portion during an inspiration phase, the annular chamber will inflate and form a seal with an inner wall of the trachea, and during an expiration phase the annular chamber will deflate and contract so as to contact the outer circumferential surface of the inside tube portion to permit air to flow between said balloon and the inner wall of the trachea to permit speech by the patient, wherein the inside tube portion includes at least one open portion is formed as a mesh, and the balloon is connected to the inside tube portion by adhering a first portion of the balloon to an outer circumferential surface of the inside tube portion above the open portion, and adhering a second portion of the balloon to an outer circumferential surface of the inside tube portion below the open portion so that air can only enter and exit the annular chamber through the open portion.

5. The tracheostomy tube as claimed in claim 4, wherein the annular chamber is externally closed.

6. The tracheostomy tube as claimed in claim 4, wherein said hollow tube has at least one hole formed in a wall of the inside tube portion, and said balloon is connected to the outer circumferential surface of the inside tube portion so that the interior of said hollow tube is communicated with the inflatable annular chamber via the hole.

* * * * *